(12) United States Patent
Gassman et al.

(10) Patent No.: US 11,387,006 B2
(45) Date of Patent: Jul. 12, 2022

(54) CLIENT MONITORING, MANAGEMENT, COMMUNICATION, AND PERFORMANCE SYSTEM AND METHOD OF USE

(71) Applicant: In Hand Health, LLC, Shawnee, KS (US)

(72) Inventors: Michael J. Gassman, Kansas City, MO (US); Jeffrey S. Clary, Overland Park, KS (US); Stephanie M. Nicholson, Leawood, KS (US); Christopher W. Maloney, Overland Park, KS (US)

(73) Assignee: In Hand Health, LLC, Overland Park, KS (US)

( * ) Notice: Subject to any disclaimer, the term of this patent is extended or adjusted under 35 U.S.C. 154(b) by 345 days.

(21) Appl. No.: 16/594,558

(22) Filed: Oct. 7, 2019

(65) Prior Publication Data
US 2020/0035367 A1     Jan. 30, 2020

Related U.S. Application Data

(63) Continuation-in-part of application No. 15/365,560, filed on Nov. 30, 2016, now abandoned.

(60) Provisional application No. 62/261,099, filed on Nov. 30, 2015.

(51) Int. Cl.
| | |
|---|---|
| *G16H 80/00* | (2018.01) |
| *G16H 20/30* | (2018.01) |
| *G06F 9/54* | (2006.01) |
| *A61B 5/00* | (2006.01) |
| *G16H 15/00* | (2018.01) |

(52) U.S. Cl.
CPC .......... *G16H 80/00* (2018.01); *A61B 5/0022* (2013.01); *G06F 9/542* (2013.01); *G16H 15/00* (2018.01); *G16H 20/30* (2018.01)

(58) Field of Classification Search
CPC ........ G16H 80/00; G16H 20/30; G16H 15/00; A61B 5/0022; G06F 9/542
USPC ....................................................... 705/2–4
See application file for complete search history.

(56) References Cited

U.S. PATENT DOCUMENTS

| | | | |
|---|---|---|---|
| 7,056,267 B2 | 6/2006 | Demas | |
| 2004/0204962 A1* | 10/2004 | Howser | A61N 1/37282 600/300 |
| 2005/0144042 A1* | 6/2005 | Joffe | G16H 10/20 705/2 |
| 2009/0221890 A1 | 9/2009 | Saffer et al. | |
| 2012/0029936 A1* | 2/2012 | Hanoun | A61B 5/103 705/2 |
| 2013/0268282 A1 | 10/2013 | Hugo et al. | |

(Continued)

*Primary Examiner* — Mark Holcomb
(74) *Attorney, Agent, or Firm* — Law Office of Mark Brown, LLC; Christopher M. DeBacker

(57) ABSTRACT

A communication, analysis, and treatment system including a computer system having a computing device associated with a specialist professional (e.g. a physical therapist) and a mobile computing device associated with a client (e.g. a patient). A remote server and database stores the software associated with the present invention. The specialist is able to quickly view a dashboard containing a brief description and status of all of the specialist's clients. In the example of a physical therapist, this would include all of the therapist's patients. Client data is organized into episodes, such as injury events. Prescriptions are assigned by the specialist to respond to these episodes. Access to this data is strictly restricted for confidentiality.

11 Claims, 18 Drawing Sheets

(56) References Cited

U.S. PATENT DOCUMENTS

| | | |
|---|---|---|
| 2014/0081661 A1 | 3/2014 | Fu et al. |
| 2014/0172460 A1 | 6/2014 | Kohli |
| 2014/0270711 A1 | 9/2014 | Maser et al. |
| 2015/0004581 A1 | 1/2015 | Selman et al. |
| 2015/0081310 A1 | 3/2015 | Keiler et al. |
| 2015/0081318 A1 | 3/2015 | Hussam |
| 2015/0088536 A1* | 3/2015 | Thelen .................. G16H 40/67 705/2 |
| 2016/0378950 A1 | 12/2016 | Reiner |

* cited by examiner

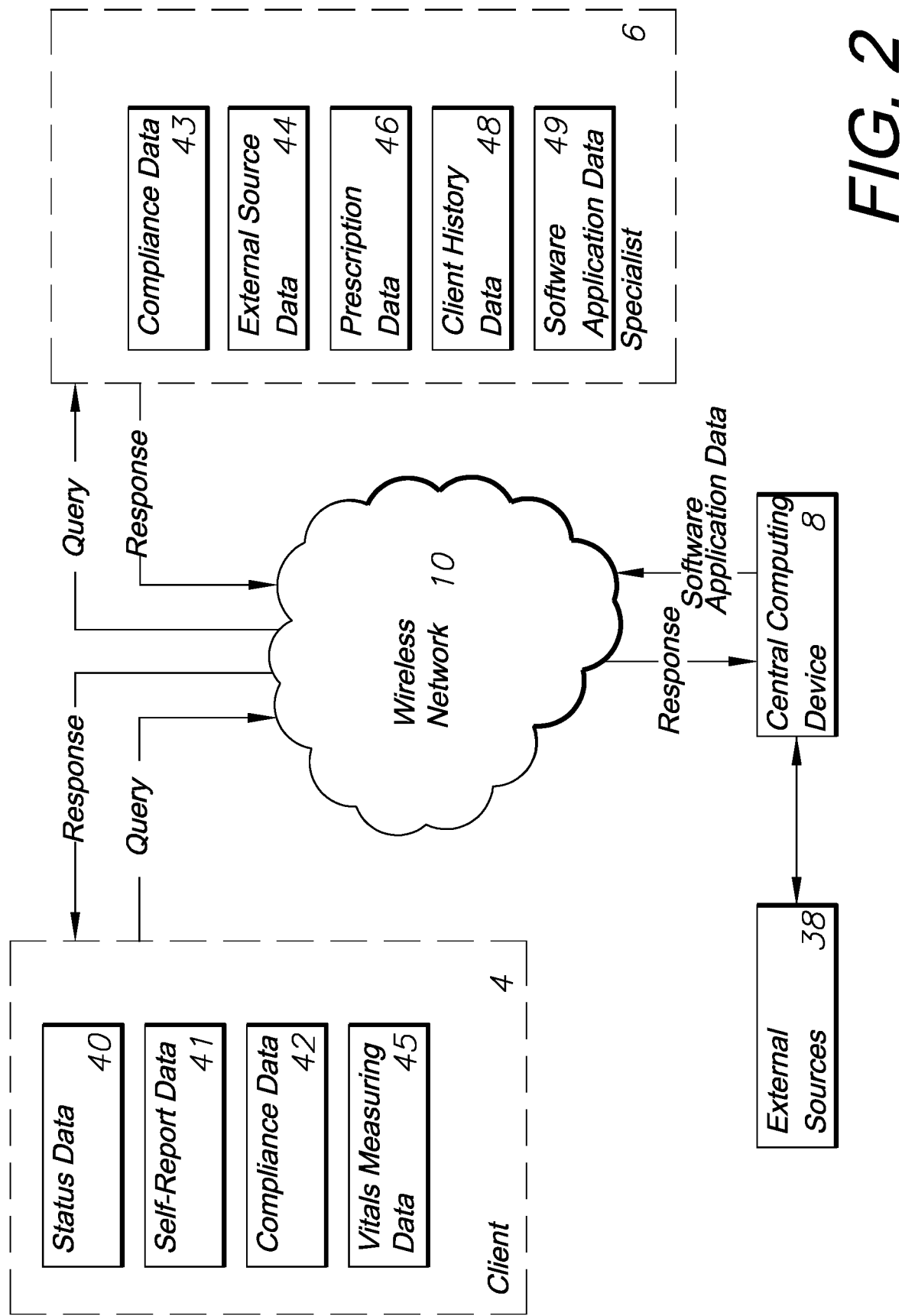

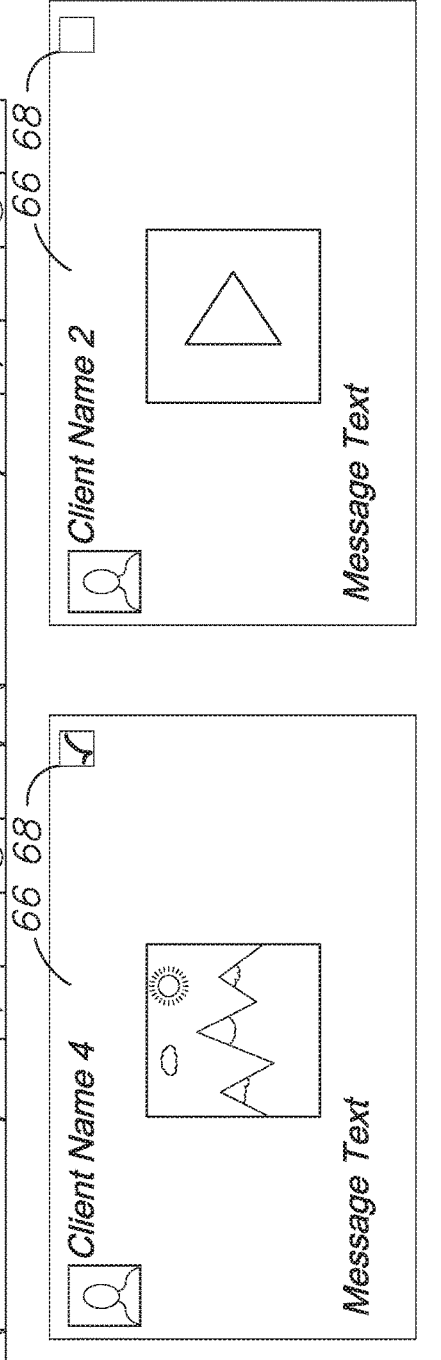

Protocol Library 70

71

72 ● Stock Protocols
74 ○ My Saved
76 ○ My Network

80 ⊕ New Protocol

Search Protocols 78

84

| Protocol #1 | Protocol Description |
| Protocol #2 | Protocol Description |
| Protocol #3 | Protocol Description |
| Protocol #4 | Protocol Description |
| Protocol #5 | Protocol Description |
| Protocol #6 | Protocol Description |
| Protocol #7 | Protocol Description |

82

Category
All... ▽

Region
All... ▽

Prescription / Diagnosis
All... ▽

Sort By  Name (A → Z) ▽

X Protocols   Get All

*FIG. 4*

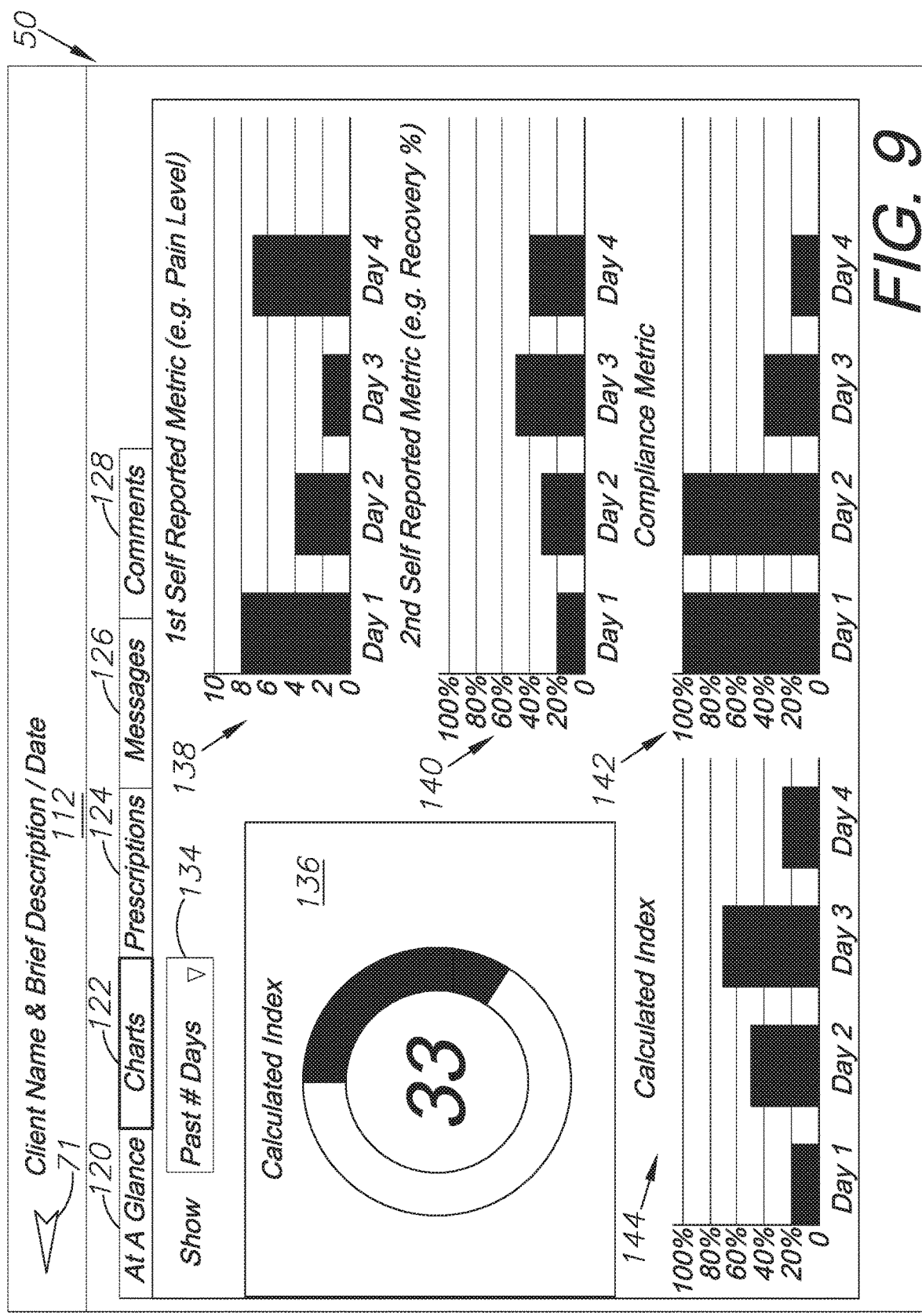

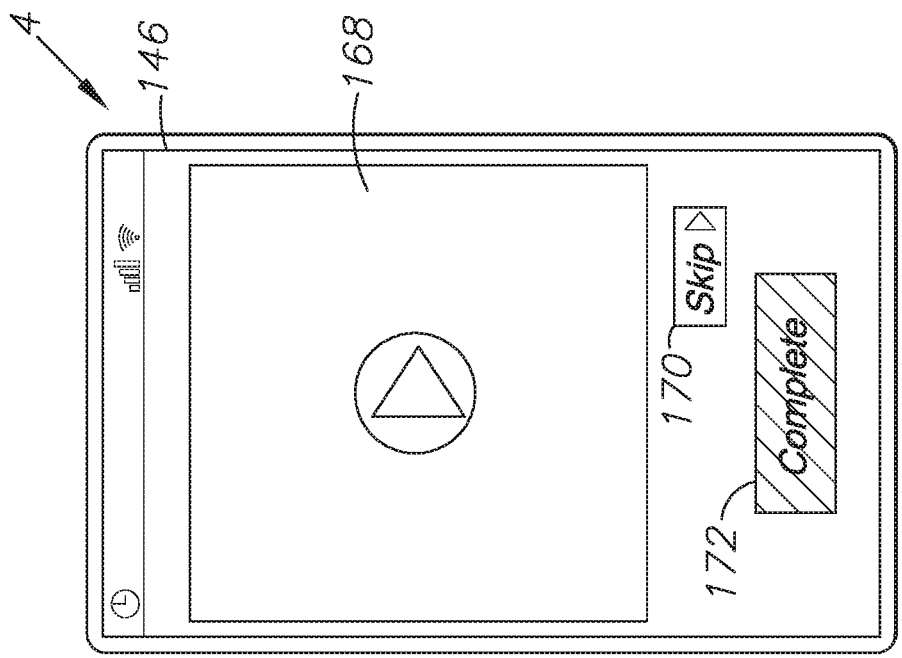

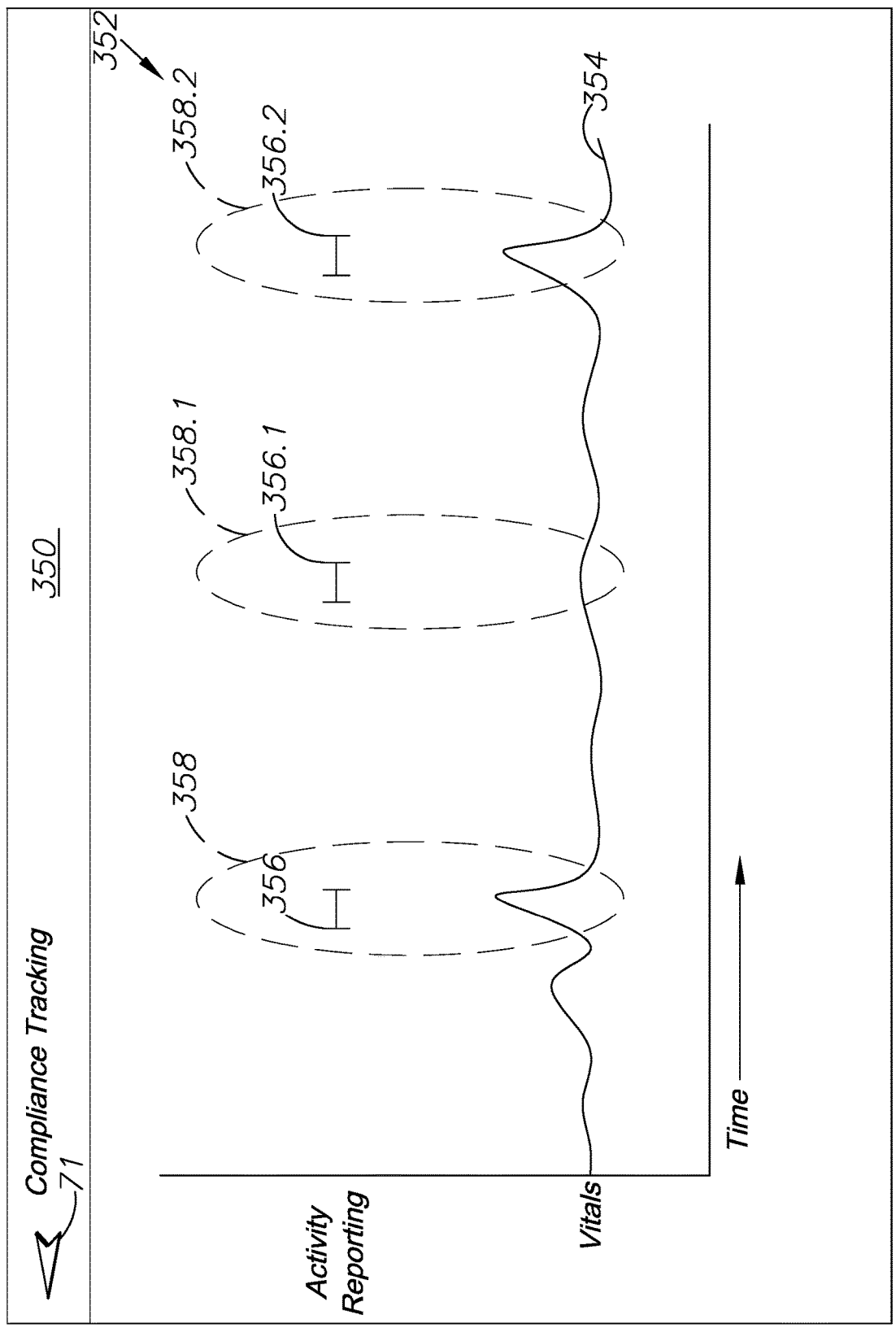

CLIENT MONITORING, MANAGEMENT, COMMUNICATION, AND PERFORMANCE SYSTEM AND METHOD OF USE

CROSS-REFERENCE TO RELATED APPLICATION

This application is a continuation-in-part of and claims the benefit of U.S. patent application Ser. No. 15/365,560 Filed Nov. 30, 2016, which claims the benefit of U.S. Provisional Patent Application No. 62/261,099, filed Nov. 30, 2015, all which are incorporated herein by reference.

BACKGROUND OF THE INVENTION

1. Field of the Invention

The present invention relates generally to a patient recovery management system and method of use thereof, and more specifically to a computer software communication tool for use between a patient or client and a physician, physical therapist, trainer, or other specialist for monitoring patient/client progress and/or recovery, providing communication between the parties, and creating and assigning prescriptions for exercises or other tasks.

2. Description of the Related Art

Physical therapists, physicians, personal trainers, and other specialists typically do much for their patients and clients during routine visits to the specialist's office. However, the time between patient or client visits is typically impossible for the specialist to monitor. Coincidentally, this time between the visits is the most crucial to patient or client recovery or progression. Many patients or clients may "fall off the wagon" during these lapses between visits and fail to completely perform tasks requested by them of their specialist, such as performing recovery exercises prescribed by a physical therapist. The reasons for these lapses are many; sometimes the exercises may be difficult for the patient to recall how to properly perform; sometimes the exercise prescription may be extensive and difficult for the patient to recall; and sometimes a lack of motivation or inability to communicate with their specialist leaves the patient or client unwilling or unable to perform their tasks completely or at all.

What is needed is a system which allows these types of specialists to easily monitor their patients and clients between visits, a system for measuring which patients are performing well and which are falling behind, and a means for allowing quick and confidential communication between patients and specialists to overcome any issues between visits.

Heretofore there has not been available a system or method for client management and communication with the advantages and features of the present invention.

SUMMARY OF THE INVENTION

The present invention generally provides a computer system including a computing device associated with a specialist professional (e.g. a physical therapist) and a mobile computing device associated with a client (e.g. a patient). A remote server and database stores the software associated with the present invention. The specialist is able to quickly view a dashboard containing a brief description and status of all of the specialist's clients. In the example of a physical therapist, this would include all of the therapist's patients.

Each of the therapist's patients will be color-coded and could be sorted by a Calculated Rehabilitation Index, or "CaRe Index," which is calculated using a weighted algorithm including data provided by the patient, data provided by the therapist, and data calculated by the server. The therapist can quickly determine which patients are having issues and why, and can evaluate which patients need immediate feedback or help.

The software system allows the therapist to generate exercise prescriptions for each of their patients. These prescriptions may include exercises loaded from prescription templates, or may be customized as the therapist deems necessary. Each prescription is then sent to the patient in the form of instructional videos which may be accessed by the patient via their mobile computing device. If each of the videos is watched in full, it is accepted that during that time, the patient has conformed with the task assigned by the therapist, and the CaRe Index is adjusted accordingly. The patient then provides feedback after the prescription is completed as to how they physically are feeling. This further adjusts the index. Notes or other information input by the therapist further adjusts the index.

HIPAA-secure therapist-to-patient messaging is provided alongside the dashboard. If a patient would like to communicate with the therapist or vise-versa, the two parties can do so using text, sound-clips, video-clips, photographs or a combination thereof. All of this communication is protected as required by HIPAA standards. Video-clips may be useful to verify that the patient is performing each exercise correctly. This further allows the therapist to check in on patients who are trending downward on the CaRe index between office visits.

BRIEF DESCRIPTION OF THE DRAWINGS

The drawings constitute a part of this specification and include exemplary embodiments of the present invention illustrating various objects and features thereof.

FIG. 2 is another block diagram depicting the relationship between other elements of the present invention.

FIG. 3 is a diagram depicting an example dashboard user interface (UI) of a specialist's computing device embodying elements of an embodiment of the present invention.

FIG. 4 is a diagram depicting an example protocol library user interface (UI) of a specialist's computing device embodying elements of an embodiment of the present invention.

FIG. 9 is a diagram depicting an example an example client description "charts" tab user interface (UI) of a specialist's computing device embodying elements of an embodiment of the present invention.

FIG. 10E is a diagram depicting an example instructional video user interface (UI) of a client's mobile computing device.

FIG. 14 is a diagram depicting an example vitals vs. compliance chart within a user interface (UI) of a specialists mobile computing device.

DETAILED DESCRIPTION OF THE PREFERRED EMBODIMENTS

I. Introduction and Environment

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning. Additional examples include computing devices such as a mobile smart device including a display device for viewing a typical web browser or user interface will be commonly referred to throughout the following description. The type of device, computer, display, or user interface may vary when practicing an embodiment of the present invention. A computing device could be represented by a desktop personal computer, a laptop computer, "smart" mobile phones, PDAs, tablets, or other handheld computing devices.

While a preferred embodiment of the present invention focuses on a system usable between a physical therapist and their patients, the present invention could be utilized in any service industry where a specialist would benefit from following up on a daily basis with their clients, such as (but not limited to) medical doctors, occupational therapists, social workers, and personal trainers.

II. Preferred Embodiment Client and Specialist Management and Communication System 2

Figure 1:
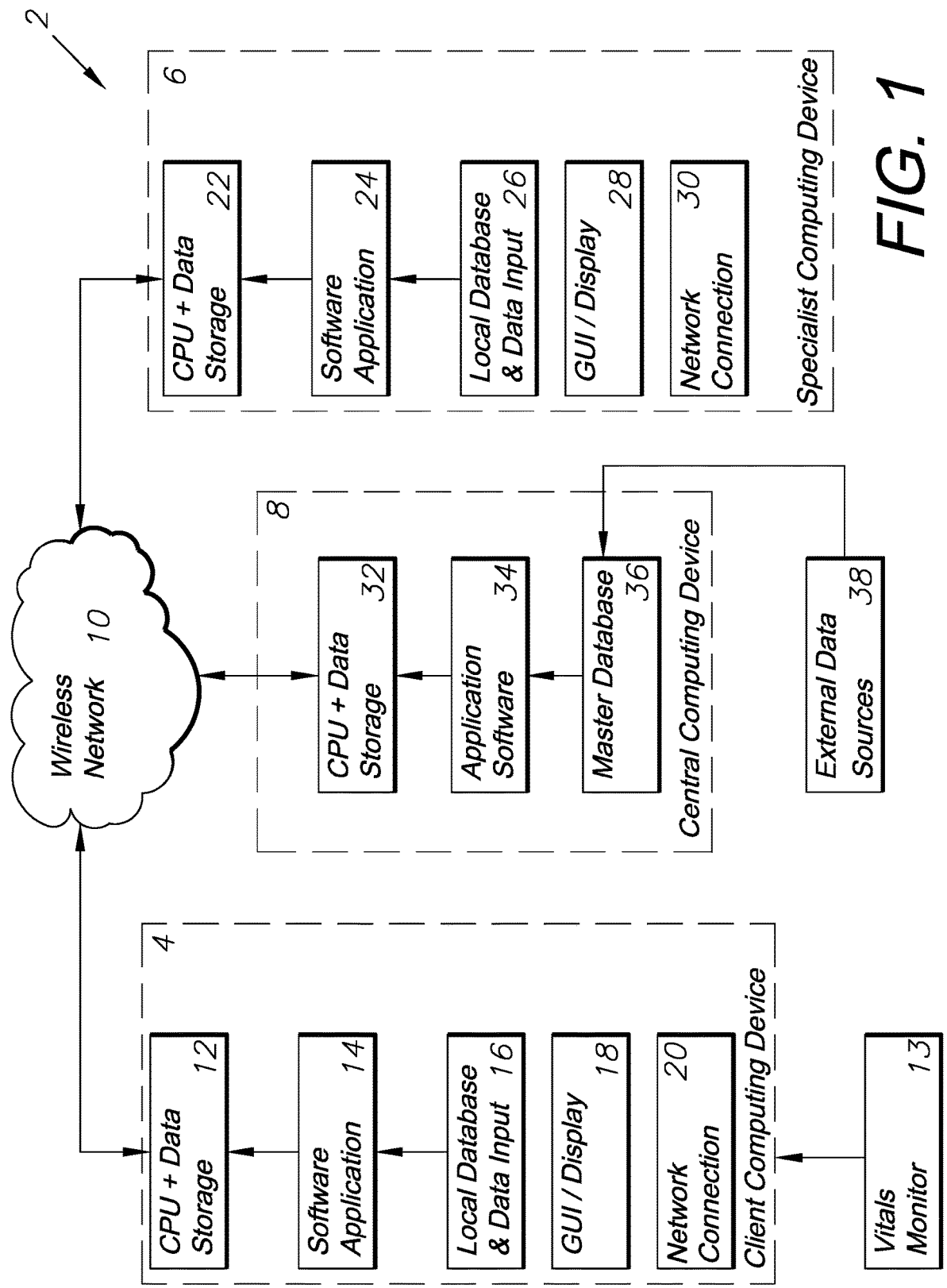
FIG. 1 is a block diagram depicting the relationship between many elements of the present invention.

Referring to the figures in more detail, FIG. 1 shows a preferred embodiment of a client and specialist management and communication system 2. A primary example of such as system would be one where the client is a patient and the specialist is a physical therapist or other medical professional, however the present invention could be used for any client-specialist communication and management relationship.

In detail, FIG. 1 shows the primary components of the management and communication system 2, including a client mobile computing device 4, a specialist computing device 6, a central computing device server 8, and a wireless communications network 10, such as the internet.

The client computing device 4 would typically be a smartphone, tablet, or personal computer. The device itself includes a CPU and data storage 12 storing and running a software application 14 for accessing the management and communication system. A database and data input 16 stored on and input into the computing device 4 is accessible with the software application 14. A graphical user interface (GUI) display 18 allows the user to interact with the software application. A network connection 20, such as an antenna, allows the device to access the wireless network 10. A vitals monitor 13, such as a wearable heart monitor, glucometer, or other vitals measuring device also communicates with the client computing device 4 for capturing vitals measuring data 45 as shown in FIG. 2. This vitals measuring data 45 received from the vitals monitor 13 can be used to determine whether the client actually performed the prescribed exercises as outlined below and more clearly described in relation to FIGS. 13 and 14.

Similarly, the specialist's computing device 6 would typically be a smartphone, tablet, or personal computer: typically both a mobile smart phone and a stationary desktop computer. The device itself includes a CPU and data storage 22 storing and running a software application 24 for accessing the management and communication system. A database and data input 26 stored on and input into the computing device 6 is accessible with the software application 24. A graphical user interface (GUI) display 28 allows the user to interact with the software application. A network connection 30, such as an antenna, allows the device to access the wireless network 10.

The central computing device 8, or central server, stores the core software, databases, and processing components for the management and communication system 8. It stores the software applications that the clients and specialists must download to access the various data pertinent to the present invention. The central server therefore includes a CPU and data storage 32, application software 34, and a master database 36. The central server may also be connected to external data sources 38, either through the wireless network 10 or otherwise.

FIG. 2 shows further interactions of data between the client device 4, the specialist device 6, and the central computing device 8 via the wireless network 10. The client device 4 stores client status data 40, self-reporting data 41, and compliance data 42. That data is sent via queries from the client's device, and responses can be sent back from the specialist's device 6. The compliance data 42 from the client device is transformed into compliance data 43 stored in the specialist's computing device, along with external source data 44, prescription data 46, client history data 48, and software application data 49.

In the example of a client-specialist relationship wherein the client is a patient and the specialist is a physical therapist, the client/patient will receive prescriptions including exercises to be performed. These will be prescribed by the specialist/therapist, and assigned via the software application. These prescriptions will include videos of exercises being performed, a set number of sets and repetitions for each exercise to be performed, and other instructional information. The client/patient will self-report several criteria each day, including pain level and level of recovery. His is the self-reported data 41. Compliance data 42 will be automatically collected as the patients confirm that the exercises have been performed. This data is sent to the specialist/therapist, and is turned into a calculated index 136 (see FIG. 9) which provides the specialist an at-a-glance view of the client's progress.

FIG. 3 shows an example user interface of a dashboard 52 associated with the software application 24 of the specialist as contained within a browser window 50, such as would be viewable on a personal computer. Here, a list of the specialists' clients can be seen at a glance, along with basic information on each client. Each client has a client photograph and client name 56 along with a brief description of the client's purpose for seeing the specialist (e.g. in the patient/therapist example, the patient's injury). Three data points are shown, such as a self-reported 1-10 pain level 58, a 1-100% level of recovery 60, and a 1-100% level of compliance 62 which is automatically calculated if the patient/client performs the prescribed exercises in that example. An arrow 64 indicates if the client is trending upwards or downwards from day-to-day. Each client bar would also be color-coordinated according with the calculated index 136, which is derived from the three data points 58, 60, 62 indicated above. The specialist can use a dropdown menu 54 to sort the list of patients as desired, such as by data point, calculated index value, or other.

Also shown on the dashboard are messages 66 sent from clients to the specialist. An indicator 68 shows if the message has been viewed or not. The messages could include photographs or videos, such as photos or videos of the patient performing exercises in accordance with an assigned prescription from the specialist.

In a preferred embodiment of the present invention, such as an example situation where the professional is a physical therapist and the client is a patient, only those therapists assigned to a particular patient will have access to the patient's information, messages, and past and present episode data. Each patient's condition is divided into a separate episode, and is treated by prescriptions comprising multiple performances (e.g. exercises) as described in more detail below. All of this data is stored on the central computing device 8, and is kept completely confidential. In the case of a medical office or physical therapist clinic, this means all communications, prescriptions, and performance history are kept HIPAA compliant. Only notifications are sent to the client's mobile computing device 4 to indicate that new prescriptions or exercises are available for view.

FIG. 4 shows a protocol library 70 user interface, which would be accessed from the dashboard 52. A back button 71 would allow the specialist to return to a previous menu or interface. In the example of a patient/client and therapist/specialist, the protocols 84 would be sets of exercise aimed at physical therapy recovery for a specific injury or post-surgery rehabilitation. New protocols can be added by the specialist at any time by accessing the new protocol button 80. There, the specialist can lump together exercises into new protocols. The specialist can browse stock protocols 72, such as those provided from the central server 8, the specialists' own saved protocols 74 which they have created, or a local network of protocols 76, such as those created by other therapists in the specialist's practice group. The protocols can be searched in the search bar 78, such as by exercise or diagnosis, or they can be sorted by category, region, etc. as identified in the sorting menu 82. Protocols are a suggested series of performances (e.g. exercises) intended for treating a particular situation or diagnoses. These protocols can be broken up into multiple steps or phases as treatment progresses. These are intended to be long-term plans for patient recovery or generalized client treatment.

Figure 5:
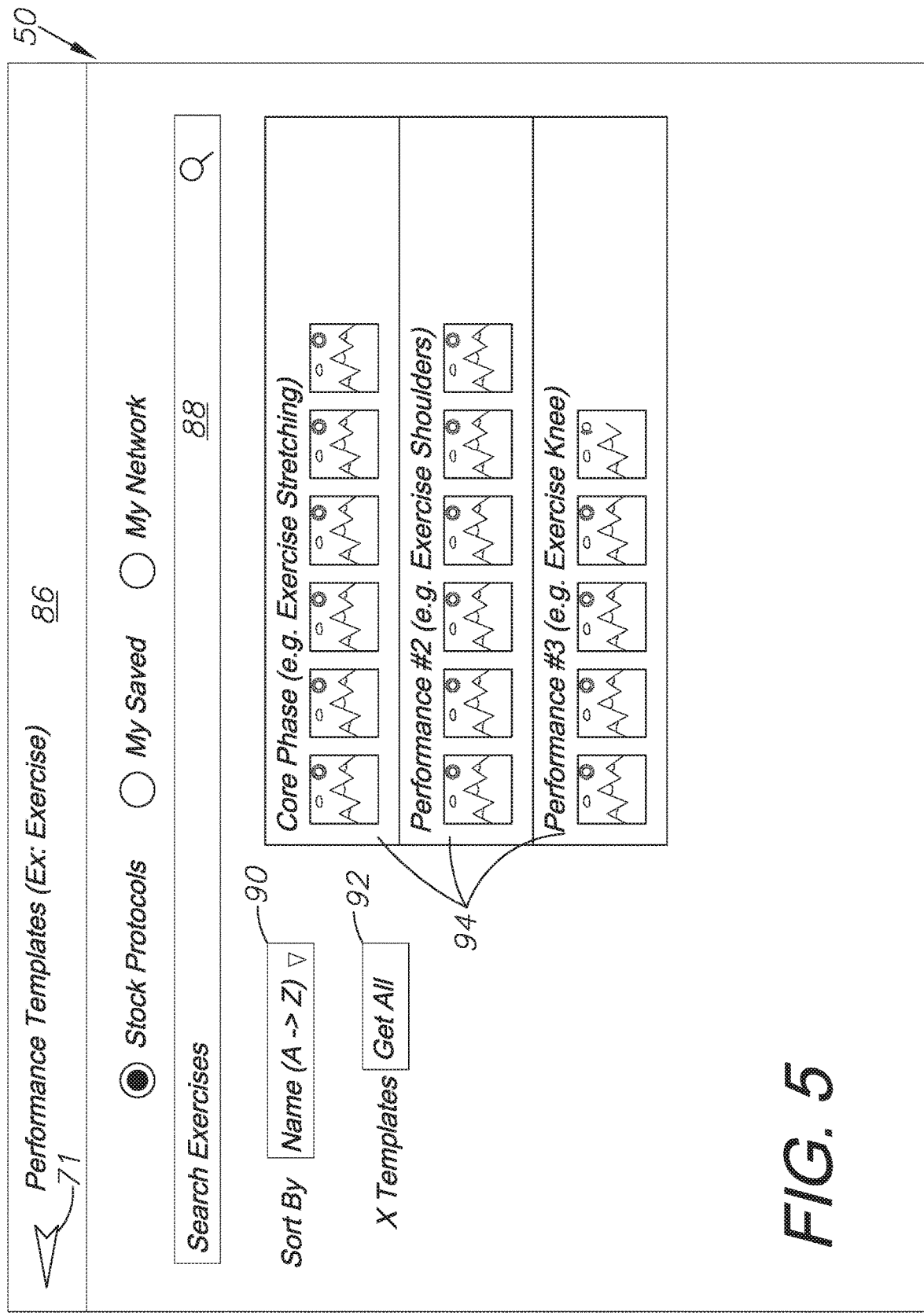
FIG. 5 is a diagram depicting an example performance template user interface (UI) of a specialist's computing device embodying elements of an embodiment of the present invention.

FIG. 5 shows a performance templates interface 86 which provides access to performances 94, such as exercises, which can be grouped together into templates 86. Individual exercises or exercise templates can then further be grouped into the protocols indicated above and shown in FIG. 4. Another search bar 88 allows for searching through the exercises, or they can be sorted by the dropdown sort menu 90 or all may be shown using the "get all" button 92. These templates 94 include the name of the template, such as what is being targeted, and may include many photographs of steps of performing the various exercises.

Figure 6:
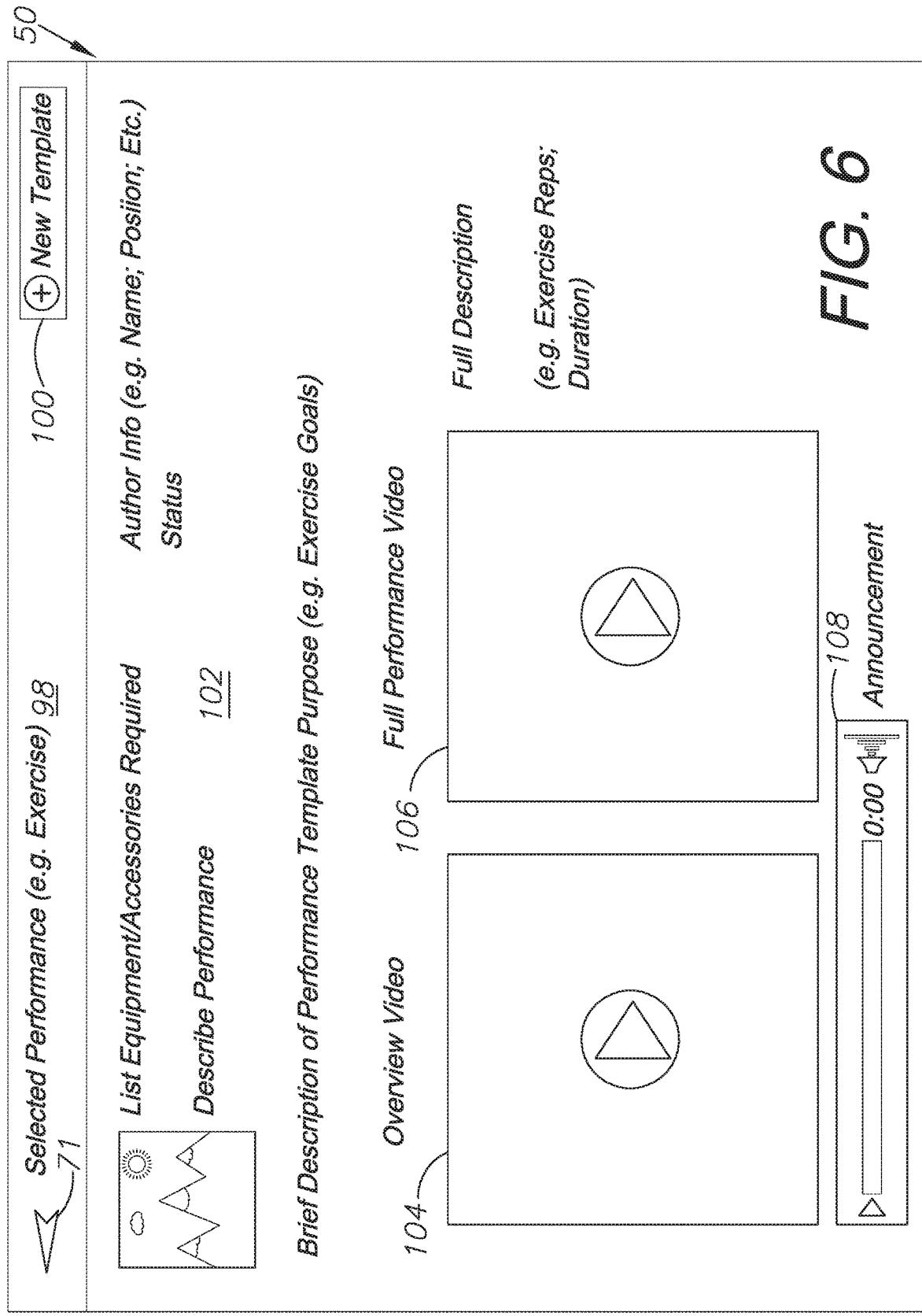
FIG. 6 is a diagram depicting an example selected performance template user interface (UI) of a specialist's computing device embodying elements of an embodiment of the present invention.

FIG. 6 shows an individually selected performance user interface 98, which can be accessed by selecting a template from the previous interface shown in FIG. 5. These performances typically include exercises to be performed by the client. New performances (e.g. exercises) or performance templates can be created at this stage using the new template button 100. The selected performance has an overview photo along with information 102 about the template, such as the author, the status, and a detailed description of the exercise(s) involved in the performance. An overview video 104 is accessible, which gives a brief overview of how the exercise is performed and what it does. An actual performance video 106 provides a full performance of the exercise, showing a person physically going through the exercise in real time with voice-over commands. An audio announcement 108 could also be located here to provide additional information or feedback to clients.

Figure 7:
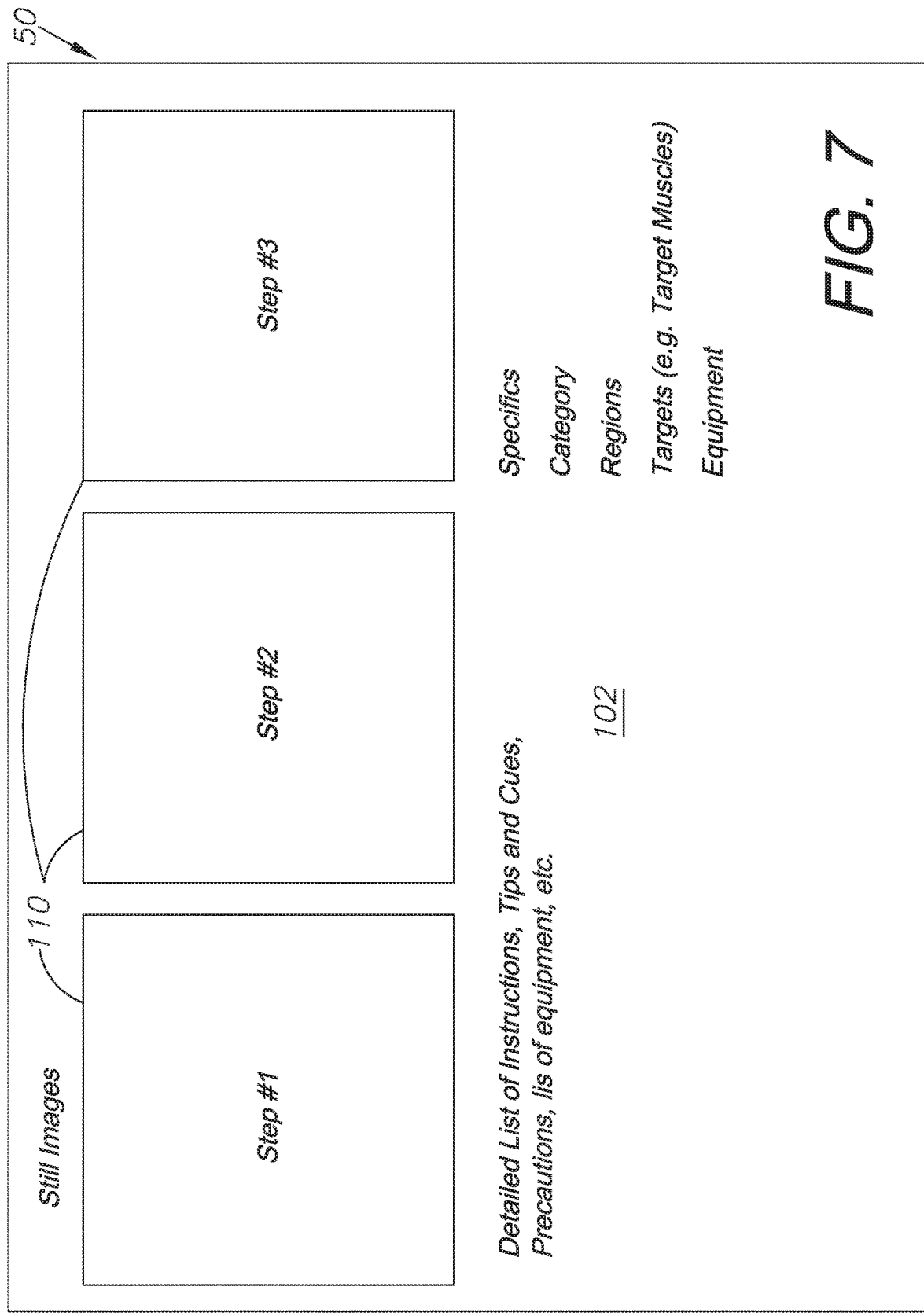
FIG. 7 is a continuation of the diagram of FIG. 6.

FIG. 7 continues the selected performance template user interface 98 from FIG. 6. Here, still images 110 of the steps of the exercise can be shown, along with more information 102 of the exercise, such as the category that the exercise is listed under, what region it is targeting, and whether any equipment is needed to perform the exercise.

Figure 8:
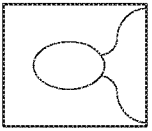
FIG. 8 is a diagram depicting an example client description "at a glance" tab user interface (UI) of a specialist's computing device embodying elements of an embodiment of the present invention.

FIG. 8 shows a client information user interface 112, which includes several tabs for different pieces of information, including an at a glance tab 120 for providing basic patient information 130 and episode information 132. Other tabs include a charts tab 122 shown in FIG. 9, a prescriptions tab 124 which may contain a list of prescriptions prescribed to this client, a messages tab 126 which will show any messages from or to this client, and a comments tab 128 for providing a comments section for the specialist to use. On the at a glance tab 120, the specialist can also choose to create a new episode 114 for the client or to close the existing episode 116 of the client, or even to edit 118 the current episode. In the example of a patient/client and a physical therapist/specialist, these episodes would likely be client visits for individual injury or surgery rehabilitation events. In a preferred embodiment of the present invention, the data shown here links to past and current episodes associated with the client, which can be accessed by the professional at any time. These episodes lead to past protocol assignments.

The charts tab 122 of the client information user interface 112 includes a calculated index 136 which is calculated based upon the data indicated previously both reported by the client and automatically generated based on compliance of the client. The calculated index 136 is displayed with a number and a graphical indicator of the result. The result would also be color coordinated. In the example of the patient/client, the higher the calculated index 136, the better recovered the patient and the less likely the specialist needs to follow up with that patient/client.

In a preferred embodiment, higher-valued calculated indexes would be green, with other colors such as yellow, orange, and then red indicating declining indexes. The colors of the calculated index 136 depend on the number shown in FIG. 9, and the client's bar shown in FIG. 3 would have a matching color, with the trend arrow 64 indicating if the client's calculated index is rising or declining over a set period of time.

The calculated index 136 and other charts on the charts tab 122 can be sorted based on a past number of days, weeks, months, etc. using the sort menu 134. Other charts shown on this tab include the first self-reported client metric chart 138 (e.g. patient pain levels), the second self-reported client metric chart 140 (e.g. patient recovery percentage), the compliance metric chart 142 (e.g. patient exercise performance), and past calculated index value chart 144.

FIGS. 10A-10E show a graphical user interface 146 of a client's mobile computing device 4, which in a preferred embodiment would be a smartphone or tablet computing device.

Figure 10B:
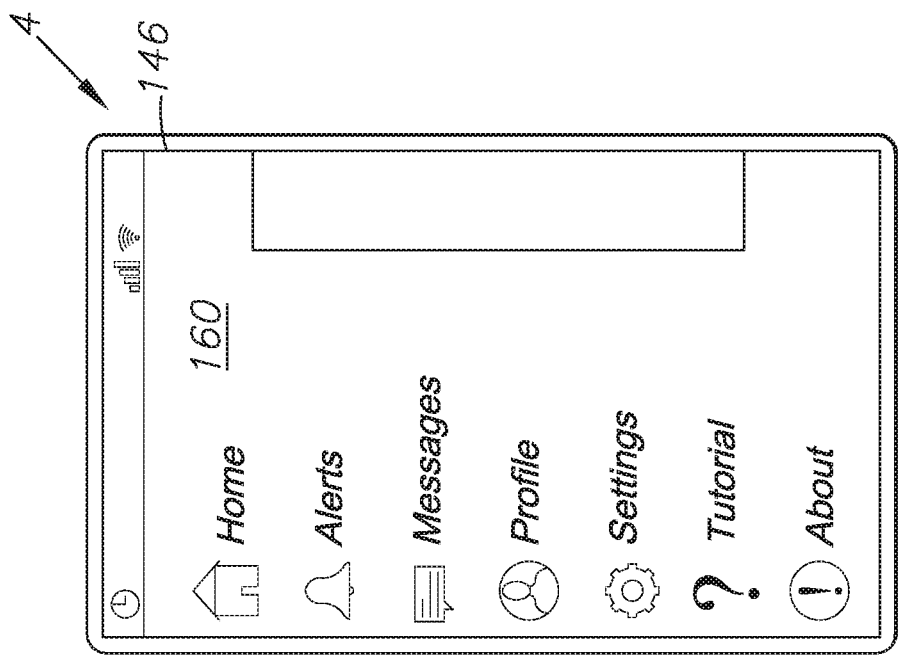
FIG. 10B is a diagram depicting an example menu user interface (UI) of a client's mobile computing device.
Figure 10A:
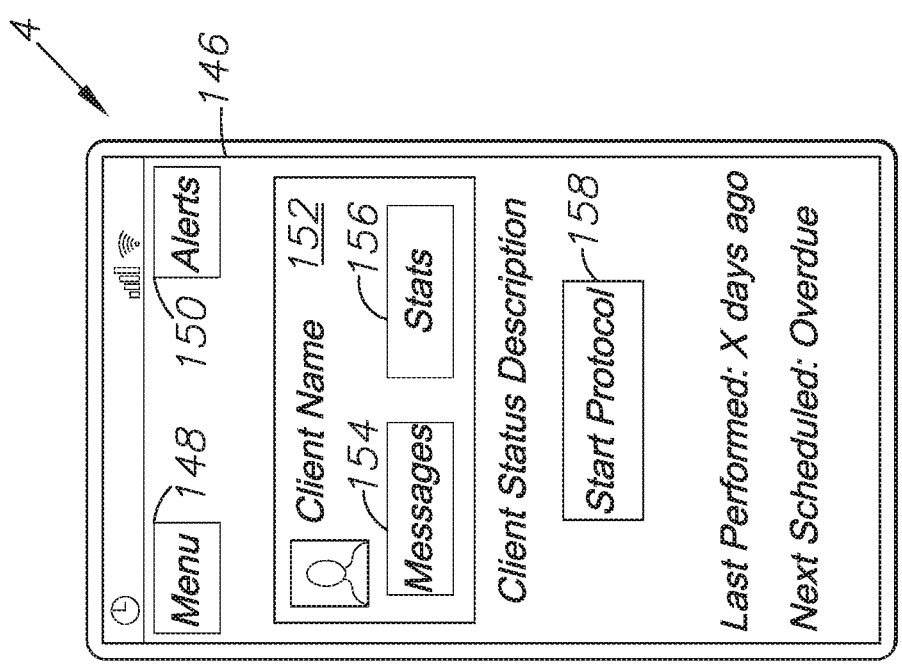
FIG. 10A is a diagram depicting an example home screen user interface (UI) of a client's mobile computing device.

FIG. 10A shows a home screen user interface with a client information window 152 identifying the client's name and optionally including a photograph of the client. Links to view messages 154 and statistics 156, such as the calculated index or other charts, are located prominently for easy access. Other links to a main menu 148 and alerts 150 are also available. Another link to begin the prescribed protocol 158 is also provided, which will take the user to a prescribed protocol (e.g. exercises). Other information, such as when the last protocol was performed or when the next protocol is due may be shown as well.

FIG. 10B shows a basic menu screen 160, which has links to many of the other portions of the software application on the client's mobile computing device 4.

Figure 10D:
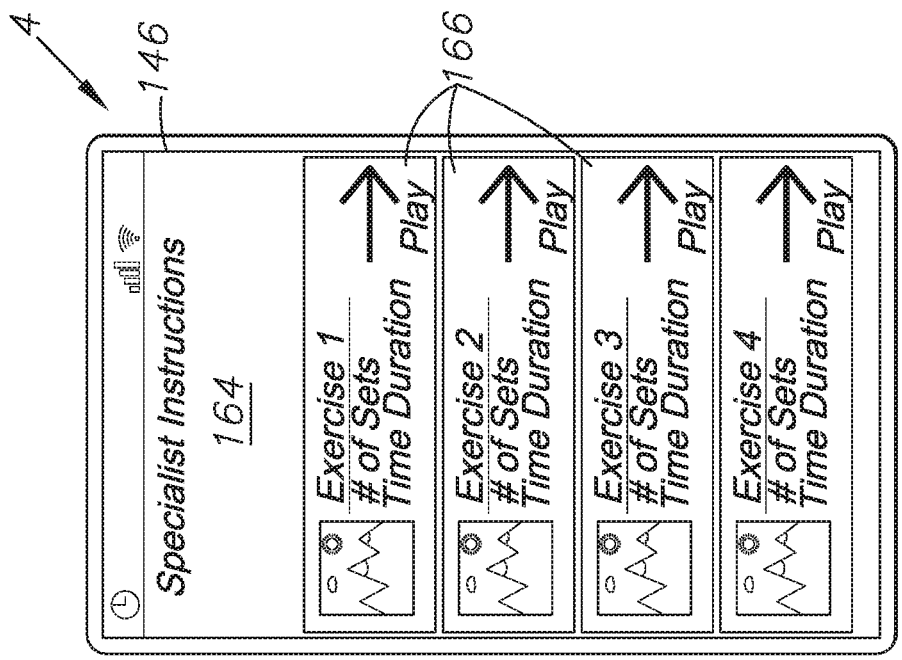
FIG. 10D is a diagram depicting an example instructions and exercises user interface (UI) of a client's mobile computing device.
Figure 10C:
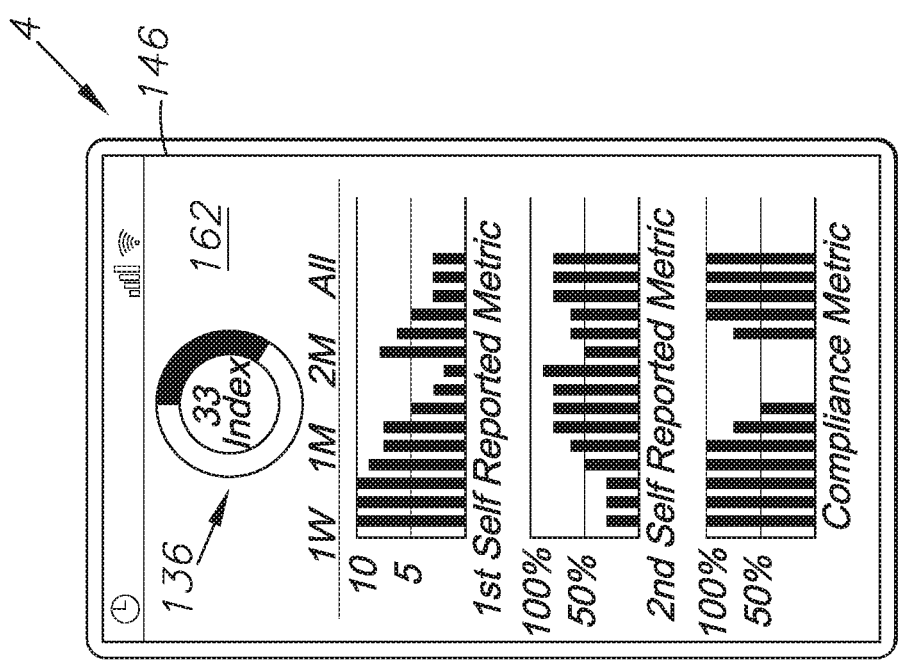
FIG. 10C is a diagram depicting an example charts user interface (UI) of a client's mobile computing device.

FIG. 10C shows a charts screen 162 similar to the interface under the charts tab 122 shown in FIG. 9. The calculated index 136 along with the other chart data can be shown here.

FIG. 10D shows an instructions screen 164 containing assigned exercises 166 from the client's specialist. These exercise links take the client to FIG. 10E which contains a video 168 of the exercise, an optional button to skip 170 the video, and a "complete" button 172 the user may activate only once the video has played completely. This is directly linked to the compliance data 42 sent from the client's mobile computing device 4 to the central server 8 and the specialist 6. This ensures the client fully views (and hopefully performs) the task shown in the video, such as in an exercise video for physical therapy recovery.

Figure 11B:
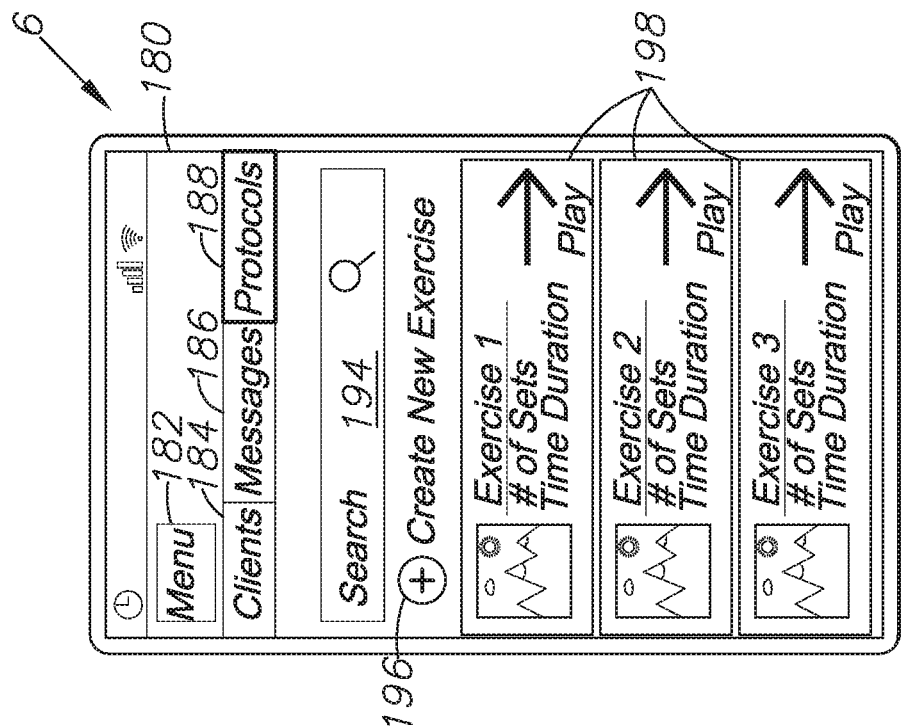
FIG. 11B is a diagram depicting an example exercises list user interface (UI) of a specialist's mobile computing device.
Figure 11A:
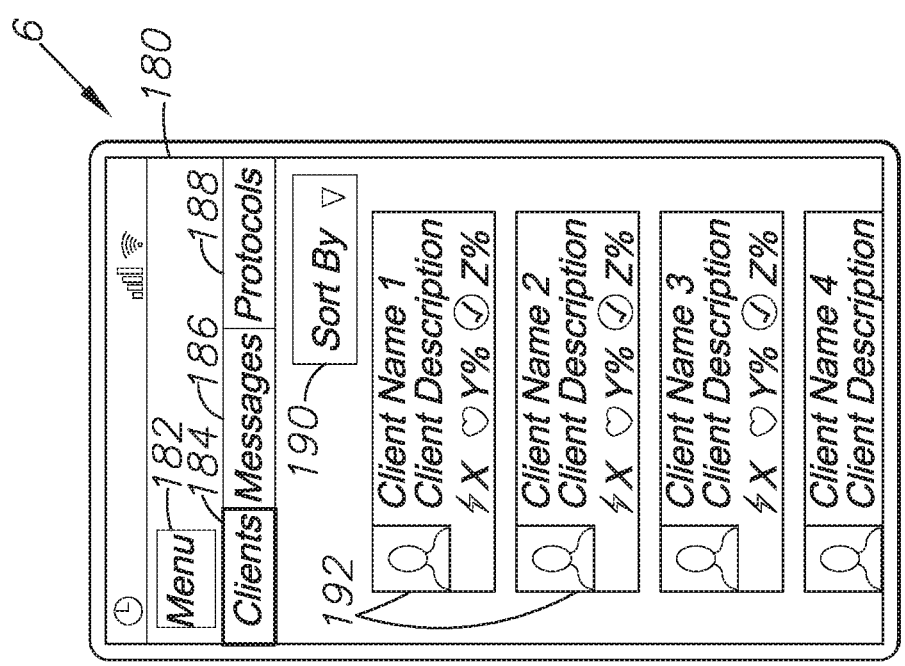
FIG. 11A is a diagram depicting an example clients list user interface (UI) of a specialist's mobile computing device.
Figure 11C:
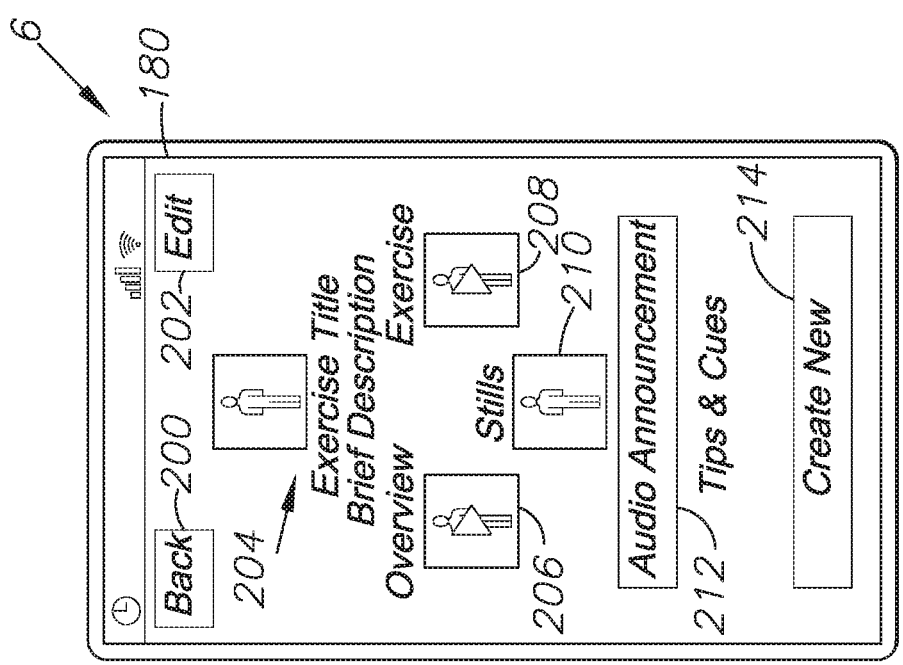
FIG. 11C is a diagram depicting an example exercise menu user interface (UI) of a specialist's mobile computing device.

FIGS. 11A-11C similarly show a user interface 180 for a specialist's mobile computing device 6, which in a preferred embodiment would be a smartphone or tablet computing device. FIG. 11A shows a list of clients 192, with a quick-display of client names, photographs, and status. The specialist can sort the list of clients using the sort dropdown menu 190. The specialist can access a basic home menu using the button 182, or can select between a clients tab 184, a messages tab 186, and a protocols tab 188 as necessary. Each tab shows different information. FIG. 11A shows the clients tab 184.

FIG. 11B shows the protocols tab 188. This tab shows a list of exercise sets 198 or other protocols which the specialist can view, edit, and assign to clients. The specialist can also create new exercises 196 using onboard components of the smartphone device 6, such as the camera and microphone. The specialist can use the search bar 194 to search for specific exercises or other protocols as well.

FIG. 11C is a view showing a selected exercise protocol 204, including a thumbnail photograph identifying the exercise, along with a brief description and title. An overview video 206 is accessible here, along with an actual exercise video 208 and photo stills 210 of the exercise. The overview video 206 provides information about the exercise, what its purpose is for, and how it is performed. The exercise video 208 actually shows the exercise being performed for a prescribed number of repetitions. An audio announcement 212 may also be included, along with other tips and cues, which may be customized for each individual client and contain more information. The specialist can back out of this screen using a back button 200, edit the exercise protocol with an edit button 202, or create a new protocol exercise with the create new button 214.

Figure 12A:
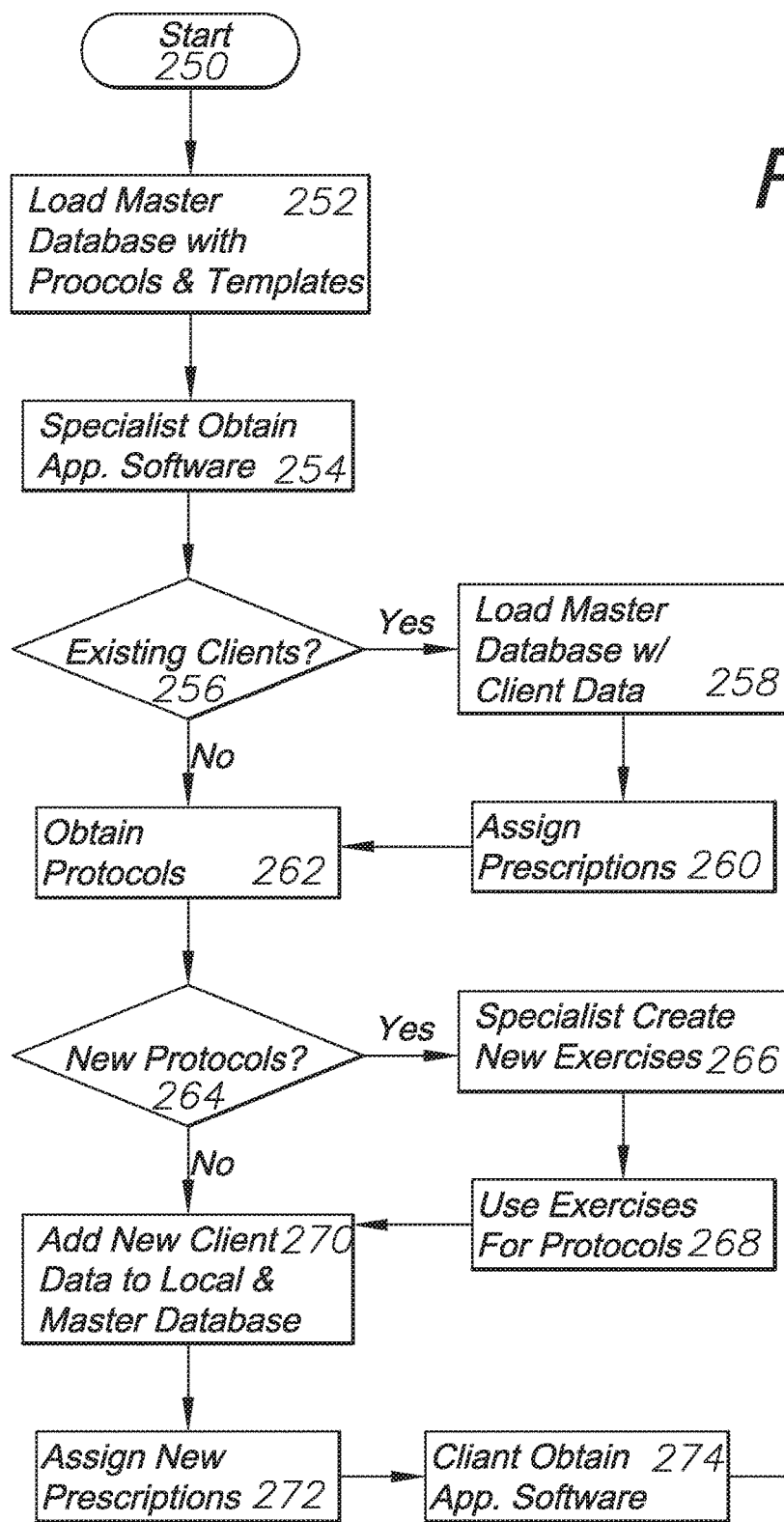
FIG. 12A is a flowchart diagramming steps taken to practice an embodiment of the present invention.
Figure 12B:
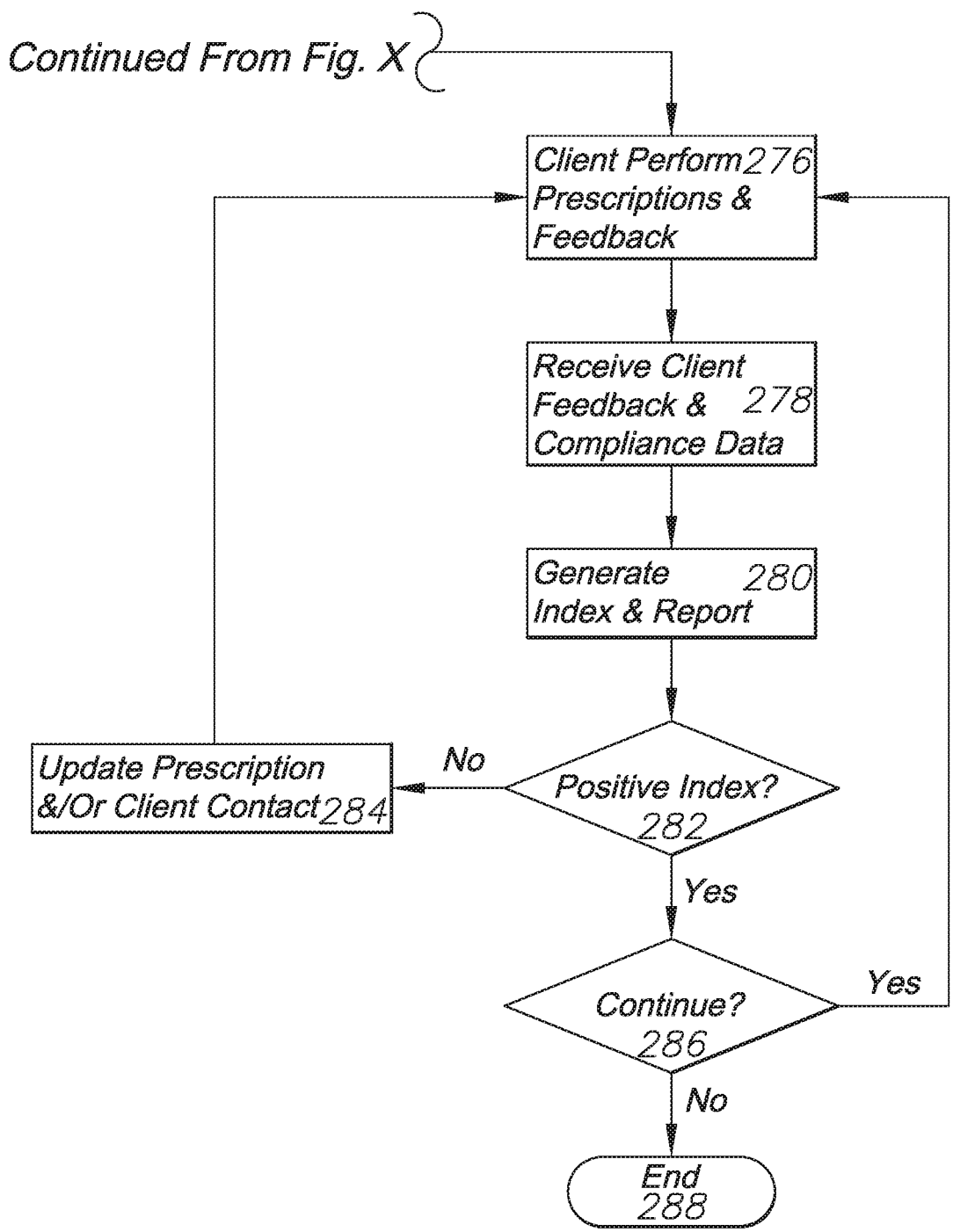
FIG. 12B is a continuation thereof.

FIGS. 12A-12B step through the process by which an embodiment of the present invention may be practiced. These steps begin at 250, after which the core master database 36 is loaded with at least some initial protocols and templates, such as the exercises and protocol templates 252 discussed above. These will form the backbone of the prescriptions which specialists can prescribe to clients until new exercises or prescriptions are created by the specialists themselves, which may be available to other specialists depending on circumstances such as client confidentiality.

Next, the specialist(s) obtains the application software at 254, whereby they download the software to their mobile computing device 6 or their personal computer, or access the software remotely using a standard internet web browser. A check occurs at 256 to determine if the specialist has existing clients whom they wish to add to the database. If yes, the master database is loaded with their client data at 258 and prescriptions that have been prescribed to those clients are assigned using the software at 260. After which the specialist obtains protocols at 262 from the master database using the software application.

The specialist can determine if new protocols should be made at 264. If yes, the specialist will create new exercises or other protocol elements at 266 as described previously. After this, these exercises and other elements are compiled into protocols at 268 which can be prescribed for clients by the specialist.

Any new clients can then be added to the local and master databases at 270, and those new clients need to have prescriptions assigned at 272. These new clients could also be existing clients requiring a new episode (e.g. new injury event for physical therapist).

All clients should then obtain the application software at 274 for receiving prescriptions from the specialist and performing the exercises, while also providing the data necessary to calculate the calculated index, allowing the specialist to monitor the client without having to have daily interaction.

Continued on FIG. 12B, the client will perform the prescriptions and provide the feedback data at 276. This leads to the calculation of the calculated index which gives the specialist information on the client's progress (e.g. recovery). The specialist and the central server receive the client feedback and compliance data at 278 and generate the index at 280, resulting in information the specialist can use to evaluate the client's status. The specialist will track the calculated index and determine at 282 if there is a positive index. If not, the specialist may opt to update the prescription and/or schedule a meeting with the client at 284 to determine what's going wrong. Otherwise, if the index is positive, the specialist will determine at 286 whether to continue the prescriptions with the client or to end the process at 288.

The present invention is not meant to be a single-pass practice, and so the example shown in FIGS. 12A and 12B are merely one example of one part of how the present invention could be practiced. In a preferred embodiment, these steps continue indefinitely as treatment is required (e.g. for a physical therapy patient).

Another important feature of the present invention is to collect data on the effectiveness of the protocols 84 and performances 94 (e.g. exercises). Data is collected from the client's self-report data 41 and compliance data 42 to indicate the effectiveness of the protocols and individual performances. As this data is collected, it can be determined how effective these protocols and performances are for treating specific episodes. This can then be used to provide feedback for other professionals looking to prescribe these protocols and performances for their own treatment prescriptions.

It should be noted that while the client computing device 4 does not necessarily include a camera and/or microphone, those features are commonly included in mobile computing devices and can provide additional features for the client to communicate with the specialist. For example, the client may take a video of themselves performing an exercise for treatment as part of a physical therapy prescription, and can message that video recording to the specialist for review. Similarly, the specialist's computing device 6 may also include a camera and microphone for recording new exercises of themselves or others for creating new protocols, as indicated above and at FIGS. 6 and 11C.

Figure 13:
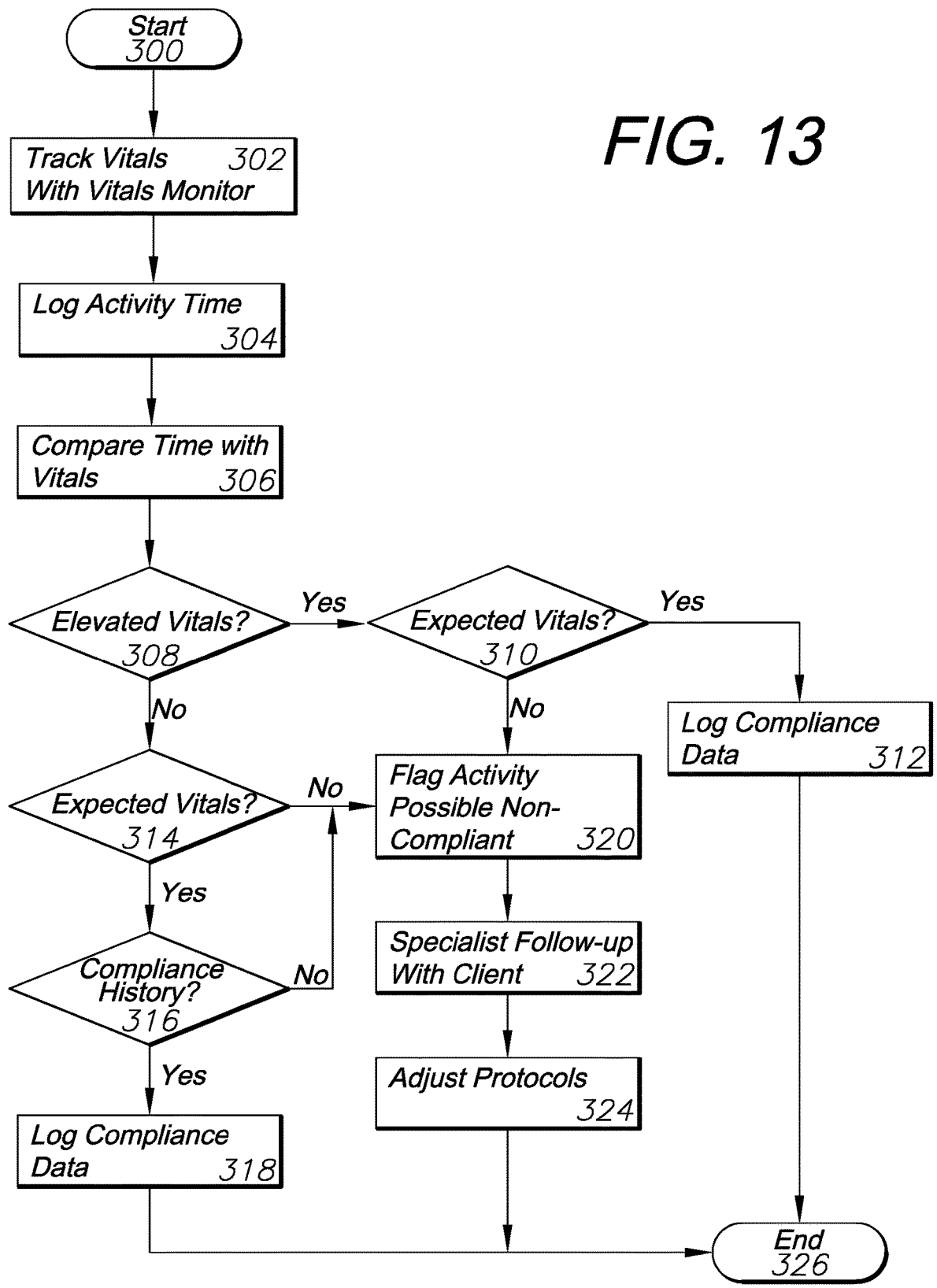
FIG. 13 is a flow chart diagramming steps take to practice an alternative embodiment of the present invention.

FIG. 13 shows how a vitals monitoring device 13 can be used to collect vitals measuring data 45 to be used to ascertain whether a client is being honest when submitting compliance data 42 into the system. The process starts at 300 where vitals measuring data is captured 302 by the vitals monitor 13. This vitals monitor could be a heart rate monitor intended to capture heartrates of the client to determine if the heartrate has increased during times when the client claims to have performed prescription exercises and submits related compliance data. Other types of vitals monitoring could include glucometers, blood pressure readings, or any other reliable and suitable vitals monitoring.

The client logs their activity time at 304, which consists of logging compliance data after performing a prescribed exercise. This activity time is compared with the logged vitals from the vitals monitoring device 13 at 306. These two are compared and a determination is made at 308 if vitals are elevated at the same time the compliance data and activity time are indicated to have been performed. If the vitals are elevated or otherwise differ from a baseline, a second comparison determines if this is an expected outcome at 310 during performance of the prescribed exercise. If yes, then the compliance data is logged at 312 into the system and the process ends at 326.

However, if there are no elevated vitals at 308, and the vitals are not expected at steps 314 or 310, the activity is flagged as possible non-compliant at 320 meaning the user may not have actually performed the prescribed exercise and merely logged that they had. A specialist must then follow up with the client at 322 and protocols may have to be adjusted at 324 to accommodate the non-compliant client. This may be requiring more in-person meetings with the specialist to address the reasons for non-compliance or even termination from the program. The process would then end at 326.

A third possibility would be whether the elevated vitals, such as heart rate, are not indicated at the indicated time of activity at 308. A check determines if this is within a realm of expected outcomes at 314, such as if the activity consists of an exercise of low effort which may not elevate vitals such as heart rate on a particular client. If this is true at 314, a further check to determine if this client has had prior compliance issues in their history at 316. If their compliance history to date has been good, the compliance data will be logged at 318 and the process ends at 326. Otherwise the activity will be flagged as possibly non-compliant at 320, resulting in specialist follow-up at 322 and protocol adjustment at 324.

FIG. 14 shows a user interface 350 comparing activity reporting against vitals tracking 352. Vitals are tracked along the line 354, which indicates a general baseline and when they might be elevated or low. Activity reporting is shown as time periods 356, 356.1, 356.2 where the client self-reports performing a prescribed exercise for a recorded period of time. A comparison window 358, 358.1, 358.2 compares the time of the recorded activity 356, 356.1, 356.2 respectively to the rate along the vitals line 354. As shown in FIG. 14, the first 358 and third 358.2 periods show elevated vitals at the time when the user self-reported compliance 356, 356.2. However, the second period 358.1 shows no significant change in the vitals line 354, while the user self-reported performing a prescribed exercise at 356.1. This would trigger the review of steps 308-324 of the flowchart in FIG. 13 to determine if the client is fraudulently self-reporting compliance and may adjust protocols accordingly.

It is to be understood that while certain embodiments and/or aspects of the invention have been shown and described, the invention is not limited thereto and encompasses various other embodiments and aspects.

Having thus described the invention, what is claimed as new and desired to be secured by Letters Patent is:

1. A prescription feedback and communications system comprising:
   a central server, a first computing device, and a second computing device, each including a respective central processing unit (CPU), data storage, graphical user interface (GUI), and a connection to a computer network;
   said data storage of said central server configured to be secured and compliant with applicable laws to protect stored data;
   said first computing device associated with a specialist and including a first microphone and a first video camera;

said second computing device associated with a client and including a second microphone, a second video camera, and a software application stored on a second data storage and accessible by a second CPU;
a prescription generated by said first computing device, said prescription comprising at least one exercise including a performance video;
said prescription sent from said first computing device through said computer network to said central server, said prescription assigned to an episode associated with said second computing device;
a notification sent from said central server through said computer network to said second computing device indicating said prescription has been received at said central server;
said prescription and said performance video configured to be accessible and viewable with said second computing device via said software application, thereby indicating completion of said at least one exercise;
compliance feedback data generated with said second computing device and sent to said central server based upon completion of said at least one exercise;
reporting data generated with said second computing device, wherein said reporting data comprises a first reporting value associated with pain level and associated with a first selected value amongst a first predetermined range, said reporting data further comprising a second reporting value associated with a recovery level and associated with a second selected value amongst a second predetermined range;
said reporting data sent from said second computing device to said central server;
a calculated index value calculated from said central server from said compliance feedback data and said reporting data, said calculated index further adjusted based upon frequency of data received from said second computing device;
said calculated index value comprising a numeric value on a scale from zero to one hundred;
said calculated index value accessible with said first computing device;
said calculated index displayed as a circular graph report having an opening on an interior space of said circular graph, and said numeric value prominently displayed within said circular graph interior space;
wherein said episode comprises a treatment problem associated with a physical ailment of a client;
wherein said prescription comprises at least one physical exercise configured to treat said treatment problem;
wherein an instructional video of said physical exercise is recorded from said first video camera of said first computing device as a recorded instruction; said recorded instruction stored on said central server;
notification of said recorded instruction sent to said second computing device; said recorded instruction is viewed on said second computing device; wherein a recorded performance video of said physical exercise is recorded from said second video camera of said second computing device;
said recorded performance video stored on said central server;
notification of said recorded performance sent to said first computing device; and
said calculated index configured to be modified based upon results of said recorded performance video.

2. The system of claim 1, further comprising:
a vitals monitoring device configured to record and wirelessly communicate client vitals with said second computing device;
a measured vitals value comprising a measurement of said client vitals at a specific time; and
a baseline vitals threshold predetermined for said client vitals, wherein a measured vitals value above said baseline threshold comprise elevated vitals, and wherein a measured vitals value below said baseline threshold comprise low vitals.

3. The system of claim 2, further comprising:
a vitals comparison generated by said CPU of said central server, said vitals comparison comprised of said measured vitals at a time corresponding with said compliance feedback; and
wherein said vitals comparison is configured to determine a likelihood of compliance.

4. The system of claim 1, further comprising:
a second prescription recorded with said first computing device and sent from said first computing device through said computer network to said central server, said prescription assigned to said episode associated with said second computing device; and
said second prescription comprising at least one customized exercise including a second performance video configured to treat said treatment problem and configured to target said client specifically.

5. The system of claim 1, further comprising:
wherein said calculated index value is represented by a pre-determined color code based upon the numerical value of said calculated index value.

6. The system of claim 1, further comprising:
said calculated index value stored on said central server;
said calculated index value comparable with previous calculated index values associated with said client stored on said central server; and
said central server configured to determine a trending direction of said calculated index value over time in a positive or negative direction, said trending direction viewable by said first computing device.

7. A computer-implemented communication method of connecting a professional with a client, the method comprising the steps:
accessing a communication system with a first computing device associated with a specialist, wherein said first computing device comprises a central processing unit (CPU), data storage, a graphical user interface (GUI), a microphone, and a camera, and wherein said communication system comprises a central server including a CPU, data storage, and a connection to a computer network;
generating a first treatment protocol associated with a client, said first treatment protocol comprising client data;
generating, with said first computing device, a first prescription and storing said first prescription on said central server, said first prescription comprising a first exercise including a first performance video diagramming said first exercise, said first prescription corresponding to said first treatment protocol;
wherein said first exercise is a customized exercise configured to target said first treatment protocol;
sending a notification to a second computing device, said second computing device associated with said client, and said notification associated with said first treatment protocol, wherein said second computing device comprises a CPU, data storage, a GUI, a microphone, and a camera;

accessing said first prescription with said second computing device; viewing said first performance video with said second computing device, thereby generating compliance data with said second computing device and transmitting said compliance data to said central server;

generating reporting data with said second computing device, said reporting data comprising a first reporting value associated with pain level and associated with a first selected value amongst a first predetermined range, said reporting data further comprising a second reporting value associated with a recovery level and associated with a second selected value amongst a second predetermined range, and transmitting said performance data to said central server;

generating a message with said second computing device, said message comprising a video performance of said exercise;

sending said message from said second computing device to said central server; sending a notification from said central server to said first computing device indicating said message has been received;

viewing said message with said first computing device;

generating a calculated index value with said CPU of said central server, said calculated index value derived from said compliance feedback data and said reporting data;

adjusting said calculated index value upon receiving additional compliance data and additional reporting data from said second computing device at said central server;

assigning a numeric value on a scale from zero to one hundred to said calculated index value;

reporting said calculated index on a circular graph report having an opening on an interior space of said circular graph, and said numeric value prominently displayed within said circular graph interior space;

accessing said calculated index value with said first computing device; and adjusting said first treatment protocol based upon said calculated index value.

8. The method of claim 7, further comprising the steps:
recording, with a vitals monitor, vitals data and transmitting said vitals data to said second computing device;
transmitting said vitals data to said first computing device;
comparing said vitals data with said compliance data;
determining whether compliance data is accurate based upon said vitals data; and
indicating accuracy of said compliance data in said reporting data.

9. The method of claim 7, further comprising the steps:
generating a second treatment protocol based upon said calculated index value;
generating, with said first computing device, a second prescription and storing said second prescription on said central server, said second prescription comprising a second exercise including a performance video diagramming said second exercise, said second prescription corresponding to said first treatment protocol; and
viewing said second performance video with said second computing device, thereby generating compliance data with said second computing device and transmitting said compliance data to said central server.

10. The method of claim 7, wherein said reporting data comprises at least a recovery value on a scale from zero percent to one hundred percent, and a pain value on a scale from zero to ten.

11. The method of claim 7, further comprising the steps:
storing calculated index value on said central server;
comparing said calculated index value with previously calculated index values associated with said single episodic event;
determining a trending direction of said calculated index with central server over time in a positive or negative direction; and
displaying said trending direction on said GUI of said first computing device, wherein said trending direction is represented by an arrow.

\* \* \* \* \*